United States Patent
Ahlers et al.

(10) Patent No.: US 9,376,360 B2
(45) Date of Patent: Jun. 28, 2016

(54) METHOD FOR STARTING UP A DME SYNTHESIS REACTOR

(71) Applicant: L'AIR LIQUIDE, SOCIETE ANONYME POUR L'ETUDE ET L'EXPLOITATION DES PROCEDES GEORGES CLAUDE, Paris (FR)

(72) Inventors: Bernd Ahlers, Dietzenbach (DE); Peter Mitschke, Maintal (DE); Joerg Herzog, Frankfurt a. M. (DE)

(73) Assignee: L'Air Liquide Société Anonyme Pour L'Étude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 14/407,517

(22) PCT Filed: Jun. 3, 2013

(86) PCT No.: PCT/EP2013/061375
§ 371 (c)(1),
(2) Date: Dec. 12, 2014

(87) PCT Pub. No.: WO2013/186072
PCT Pub. Date: Dec. 19, 2013

(65) Prior Publication Data
US 2015/0175512 A1  Jun. 25, 2015

(30) Foreign Application Priority Data
Jun. 15, 2012 (DE) .......................... 10 2012 105 212

(51) Int. Cl.
| | |
|---|---|
| *C07C 41/09* | (2006.01) |
| *B01J 8/02* | (2006.01) |
| *B01J 21/04* | (2006.01) |
| *B01J 35/04* | (2006.01) |
| *B01J 35/02* | (2006.01) |

(52) U.S. Cl.
CPC . *C07C 41/09* (2013.01); *B01J 8/02* (2013.01); *B01J 8/0285* (2013.01); *B01J 21/04* (2013.01); *B01J 35/04* (2013.01); *B01J 35/02* (2013.01); *B01J 2208/00061* (2013.01); *B01J 2208/00539* (2013.01); *B01J 2208/027* (2013.01)

(58) Field of Classification Search
None
See application file for complete search history.

(56) References Cited

U.S. PATENT DOCUMENTS 2,014,408 A  9/1935 Woodhouse et al.

FOREIGN PATENT DOCUMENTS

| | | | |
|---|---|---|---|
| DE | 3817816 A1 | 11/1989 | |
| DE | 102009053357 A1 * | 5/2011 | ............. B01J 21/04 |
| EP | 2022774 A1 | 2/2009 | |
| JP | 2004161672 A * | 6/2004 | ............. C07B 61/00 |
| WO | WO 2011095270 A1 | 8/2011 | |

OTHER PUBLICATIONS

Xu M et al: "Synthesis od dimethyl ether (DME) from methanol over solid-acid catalysts", Applied Catalysis, vol. 149, No. 2, Feb. 6, 1997, pp. 289-301, XP004338018.

* cited by examiner

*Primary Examiner* — Rosalynd Keys
(74) *Attorney, Agent, or Firm* — Justin K. Murray

(57) ABSTRACT

A method for starting up a DME synthesis reactor in which methanol is converted by dehydration to dimethyl ether on a solid catalyst, wherein the catalyst is heated up with condensing methanol vapor, possibly in several steps. In a final treatment step with superheated methanol vapor, the catalyst is dried and its temperature is raised to the starting temperature of the methanol dehydration.

21 Claims, No Drawings

METHOD FOR STARTING UP A DME SYNTHESIS REACTOR

CROSS-REFERENCE TO RELATED APPLICATIONS

This application is a U.S. National Stage Application under 35 U.S.C. §371 of International Application No. PCT/EP2013/061375 filed on Jun. 3, 2013, and claims benefit to German Patent Application No. DE 10 2012 105 212.3 filed on Jun. 15, 2012. The International Application was published in English on Dec. 19, 2013, as WO 2013/186072 under PCT Article 21(2).

FIELD

This invention relates to a method for starting up a reactor for the production of dimethyl ether (DME) by acid-catalyzed dehydration of methanol in the gas phase on solid catalysts.

BACKGROUND

The catalytic production of dimethyl ether (DME) from methanol by catalytic dehydration has been known for many years. The U.S. Pat. No. 2,014,408 for example describes a process for the production of DME from methanol on catalysts such as aluminum oxide, titanium oxide and barium oxide, with temperatures of 350 to 400° C. being preferred.

Further information on the prior art and on the current practice of the production of dimethyl ether can be found in Ullmann's Encyclopedia of Industrial Chemistry, Sixth Edition, 1998 Electronic Release, keyword "dimethyl ether". In Chapter 3 "Production" it is explained in particular that the catalytic conversion of evaporated methanol usually is carried out in fixed-bed reactors.

From the point of view of reaction engineering, fixed-bed reactors preferably are used for the catalytic dehydration of methanol to DME in the gas phase, since they are characterized by constructive simplicity. The German laid-open publication DE 3817816 for example describes a process integrated in a methanol synthesis plant for producing dimethyl ether by catalytic dehydration of methanol without previous separation of the synthesis gas not converted in the methanol reactor. As dehydration reactor a simple fixed-bed reactor is used.

The dehydration of methanol to dimethyl ether according to the reaction equation $$2CH_3OH = (CH_3)_2O + H_2O.$$

is an exothermal equilibrium reaction. Hence it follows that from a thermodynamic point of view high degrees of conversion are achieved at reaction temperatures as low as possible. On the other hand, from a reaction-kinetic point of view a minimum reaction temperature is required, in order to ensure sufficient reaction rates and thus acceptable methanol conversions. In the literature, this minimum reaction temperature also is referred to as starting temperature or light-off temperature and is dependent on the type and quality of the catalyst used, but also on the definition of an acceptable minimum conversion. During start-up of a DME synthesis reactor, it hence is required to first set this minimum temperature. As soon as the dehydration of methanol has started by forming DME, the minimum temperature can be maintained due to the exothermal release of heat or the reactor temperature even can rise further. Therefore, it often is advisable to equip the fixed-bed reactor with additional cooling devices, in order to avoid too high reactor temperatures. The same on the one hand can damage the catalyst and on the other hand can lead to the formation of by-products, such as carbon monoxide CO, carbon dioxide $CO_2$, hydrogen $H_2$ and methane $CH_4$. The formation of these by-products is undesirable, since they impair the purity of the reaction product and reduce the selectivity of the reaction to DME.

To adjust the above-described light-off temperature or starting temperature, it so far has been common practice to charge the fixed bed of the dehydration catalyst arranged in the reactor interior with a tempered inert gas stream, in order to heat up the catalyst bed by means of convective heat transfer. The heat-up temperature must be controlled carefully, in order to avoid a damage of the catalyst or sensitive plant sections due to an excessive temperature. Furthermore, just like in the synthesis operation of the reactor, a minimum flow velocity of the inert gas through the reactor should not be fallen short of, so that a uniform traversal and hence heat-up of the catalyst bed is ensured.

As inert gas, nitrogen frequently has been used so far, which in turn has been heated up by heat exchange for example against superheated steam. In DME synthesis plants integrated into a plant complex, which also includes an air separation unit, a large nitrogen stream can be provided for a short period without great expenditure. For a large DME synthesis plant, up to 100000 $m_N^3/h$ of nitrogen must be provided for a short time, when the nitrogen is passed through the synthesis reactor in straight passage when heating up the catalyst bed. Because of the poor heat transfer between the dry inert gas and the catalyst bed, this large amount of nitrogen must be heated up to a temperature above the starting temperature to be adjusted. For this purpose, a correspondingly large heat exchanger must be provided, which correspondingly increases the apparatus expenditure.

When no air separation unit is available, the provision of large amounts of nitrogen is difficult. Alternatively, the heated inert gas stream then can also be guided in a cycle, for which purpose however an additional cycle compressor is required. Since the trouble-free operation of the DME synthesis plant often can last a few years, an additional expensive and rarely used apparatus thus must be provided.

SUMMARY

An aspect of the invention provides a method for heating up a catalytic fixed-bed reactor configured to convert methanol to dimethyl ether (DME), the method comprising: (a) adjusting a catalytic fixed-bed reactor, comprising a solid catalyst suitable for dehydrating methanol to DME, to an initial temperature of the solid catalyst at a first pressure, at least one temperature measuring device being mounted in the presence of the catalyst; (b) evaporating liquid pure methanol in an evaporation device, to obtain a first vaporous pure methanol stream; (c) contacting the first vaporous pure methanol stream with the catalyst, until a condensation temperature of the methanol is reached at the first pressure, to obtain a liquid condensate comprising methanol; (d) providing the liquid condensate to a separating device, the separating device being in fluid connection with the catalyst, and discharging a condensate stream comprising methanol from the separating device; (e) lowering the pressure in the catalytic fixed-bed reactor to a second pressure, the second pressure being below the first pressure, and contacting the catalyst with a second vaporous pure methanol stream suitable for removing condensed methanol, wherein the second vaporous pure methanol stream is superheated with respect to the second pressure; (f) heating up the second vaporous pure methanol stream using a heating device, to obtain a vaporous, superheated pure methanol stream, and contacting the vaporous, superheated pure methanol stream with the catalyst, wherein the vaporous, superheated pure methanol stream is heated up to such an extent that in or at the catalyst a fixed end temperature is reached.

DETAILED DESCRIPTION

An aspect of the present invention therefore provides a method for starting up, in particular for heating up a reactor for the production of dimethyl ether (DME) by acid-catalyzed dehydration of methanol in the gas phase on solid catalysts, which is characterized by a low expenditure of required resources and apparatuses.

An aspect of the invention provides a method for starting up a reactor for the production of dimethyl ether (DME) by acid-catalyzed dehydration of methanol in the gas phase on solid catalysts, in particular on the basis of alumina, which is characterized by a low expenditure of required resources and apparatuses, a plant for carrying out such a method, as well as a DME production method, in which the DME synthesis reactor has been brought to the required reaction temperature for the dehydration of methanol with such a heating method.

An aspect of the invention provides a method for heating up a catalytic fixed-bed reactor for the conversion of methanol to dimethyl ether (DME) from an initial temperature to a fixed end temperature, wherein the catalytic fixed-bed reactor contains a solid catalyst active for the methanol dehydration to DME. A method according to the invention comprises the following method steps:
  (a) providing the catalytic fixed-bed reactor with an initial temperature of the solid catalyst at a first pressure, wherein in or at the catalyst at least one temperature measuring device is mounted,
  (b) providing a vaporous pure methanol stream by evaporating liquid pure methanol in an evaporation device,
  (c) contacting the vaporous pure methanol stream with the catalyst, until the condensation temperature of the methanol is reached at the first pressure,
  (d) providing a separation device for liquid condensate containing methanol, which is in fluid connection with the catalyst, and discharging a condensate stream containing methanol from the separation device,
  (e) lowering the pressure in the fixed-bed reactor to a second pressure below the first pressure and contacting the catalyst with a vaporous pure methanol stream for removing condensed methanol, wherein the vaporous pure methanol stream is superheated with respect to the second pressure,
  (f) heating up the vaporous pure methanol stream by means of a heating device and contacting the vaporous, superheated pure methanol stream with the catalyst, wherein the pure methanol stream is heated up to such an extent that in or at the catalyst the fixed end temperature is reached.

Pure methanol is understood to be methanol which corresponds to the purity requirements of the International Methanol Producers & Consumers Association (IMPCA) or the purity designation Grade AA (see Ullmann's Encyclopedia of Industrial Chemistry, Sixth Edition, 1998 Electronic Release, keyword "Methanol", 7. Quality Specifications and Analysis, Table 5: Federal specifications for pure methanol in the United States). For the heating method according to the invention it is important that the low water contents in the pure methanol defined there are maintained. Both in the IMPCA specification and in the purity designation Grade AA this corresponds to a maximum water content of 0.1 wt-%. It has been found that methanol with an increased water content is unsuitable for carrying out the method according to the invention, since condensing and/or adsorbing or absorbing water will damage the catalyst or impair its effectiveness.

An aspect of the invention provides a method for the production of dimethyl ether (DME) by heterogeneously catalyzed dehydration of a gaseous or vaporous feed stream containing methanol on a solid catalyst active for the dehydration of methanol to DME, which comprises the following steps:
  (a) providing a gaseous or vaporous feed stream containing methanol,
  (b) catalytic conversion of the feed stream containing methanol under dehydration conditions to obtain a product stream containing DME,
  (c) recovering the DME from the product stream containing DME,
wherein the method according to the invention is characterized in that the catalytic fixed-bed reactor is heated up before carrying out the DME production by a method as discussed above.

Suitable dehydration conditions and methods for recovering the DME from the product stream containing DME are described sufficiently in the prior art. The skilled person will adapt these instructions to the respective specific method conditions by routine experiments.

An aspect of the invention provides a plant for heating up a catalytic fixed-bed reactor for the conversion of methanol to dimethyl ether (DME), comprising the following plant sections:
  (a) a fixed-bed reactor containing a solid methanol dehydration catalyst, which is equipped with a first pressure maintaining device and at least one temperature measuring device,
  (b) a methanol evaporation device, which is equipped with a second pressure maintaining device,
  (c) a separating device for liquid condensate containing methanol, which is in fluid connection with the solid methanol dehydration catalyst,
  (d) a return conduit for recirculating liquid condensate containing methanol from the separating device to the methanol evaporation device, wherein the return conduit is in fluid connection with the separating device and the methanol evaporation device.

Fluid connection is understood to be any kind of connection which enables a fluid, for example methanol-containing condensate, to flow from the one to the other of said regions, regardless of any interposed regions or components or possibly required conveying devices.

The invention is based on the surprising finding that methanol condensing on the catalyst bed can be used as heat transfer medium for heating up the DME synthesis reactor without any impairments of the dehydration catalyst. The skilled person normally will try to avoid such condensations, as it is to be feared that active centers on the catalyst surface will be deactivated thereby. This is particularly true for catalysts whose effectiveness is based on their acidic properties, as is the case in the catalysts used for the dehydration of methanol to DME. Such catalyst surfaces show interactions with polar substances such as for example methanol already at low temperatures. Surprisingly, it has been found that the contact of the dehydration catalyst with condensed, anhydrous or water-poor pure methanol according to the purity requirements discussed above does not lead to an impairment of the catalytic effectiveness.

It is particularly advantageous that for the DME synthesis operation of the reactor superheated methanol anyway must be provided as feedstock. Correspondingly, the equipment for evaporating and superheating the methanol before entry into the reactor anyway is available in the plant. Providing large amounts of heated inert gas and/or an additional cycle compressor thus can be omitted.

The procedure of heating up the DME synthesis reactor by means of methanol vapor can be carried out as follows. In a first step, vaporous methanol is passed to the DME synthesis reactor, which condenses on the still cold catalyst surface and heats up the same via the condensation heat released. During the heating phase, the methanol leaves the reactor or the separating device integrated into the reactor or provided downstream of the same at least partly in liquid form and can be recirculated to the methanol evaporation via a return conduit. In the superheating phase, the methanol leaving the reactor in vaporous form can be condensed in succeeding apparatuses, for example distillation columns, and be recirculated to the methanol evaporation. In this way, no loss of methanol feedstock occurs.

It is particularly preferred when the method steps (b) to (d) are repeated several times when carrying out the method according to the invention, wherein the pressure is increased incrementally. In several stages, the pressure thus is raised to a pressure which is greater than the first pressure. The associated advantage consists in that in this way the catalyst temperature is increased incrementally and the occurrence of large temperature jumps is avoided, whereby the thermal load of the catalyst is reduced.

It is furthermore advantageous when the end temperature in method step (f) corresponds to the light-off temperature or starting temperature of the methanol dehydration to DME at the fixed reactor pressure. In this way, switching to the DME synthesis operation can be effected without any further preparatory measures.

An advantageous aspect of the method according to the invention provides that the solid catalyst is present in the form of a bed of granular catalyst or as catalyst honeycomb. In most cases a catalyst bed will be preferred, since the trade provides a multitude of suitable catalysts in the form of catalyst grains or particles. Solid catalysts which contain alumina, in particular γ-alumina, are particularly suitable. At higher reactor throughputs, however, the use of catalyst honeycombs may be advantageous due to the then lower pressure loss.

In a further preferred aspect of the method and reactor according to the invention it is provided that in the reactor a separating device is integrated, via which methanol condensed in the heating phase is recirculated from the fixed-bed reactor to the evaporation device. For this purpose, a return conduit is provided between the separating device integrated into the reactor and the methanol evaporation device, which possibly is completed by a conveying device, for example a pump. In this way, the methanol previously utilized for heating can be converted to the target product DME in the succeeding synthesis operation of the reactor. A disposal of the heating or heat transfer medium thus can be omitted. Alternatively, however, the separating device can also be arranged outside the reactor, as long as it is in fluid connection with the catalyst bed. This provides advantages as regards the variability of the arrangement and the constructive simplicity of the plant sections.

Further developments, advantages and possible applications of the invention can also be taken from the following description of exemplary embodiments and numerical examples. All features described form the invention per se or in any combination, independent of their inclusion in the claims or their back-reference.

Exemplary Embodiment

The following exemplary embodiment describes the start-up of a DME synthesis reactor in a pilot plant by the method according to the invention. The reactor was filled with commercially available methanol dehydration catalyst of Süd-Chemie AG on the basis of γ-alumina in extrudate form and inert ceramic spheres, which are arranged before and after the catalyst bed and serve to render the flow more uniform. The catalyst bed enclosed a central measuring tube for an axially movable thermocouple, so that the temperature of the catalyst bed could be measured at arbitrary points in longitudinal direction of the catalyst bed. Alternatively, a multi-point thermocouple can also be used. Before starting up, the reactor was rendered inert with nitrogen and was at ambient temperature and at a pressure of 6 bar. All pressures mentioned above and in the following are meant to be absolute pressures, unless otherwise indicated.

Heating up the DME reactor with condensing methanol: Pure methanol of the degree of purity Grade AA was evaporated at 8 bar. The evaporated methanol was passed to the DME synthesis reactor, where it was condensed in contact with the cold catalyst. The catalyst bed was heated continuously proceeding from the inlet side to the outlet side, and the condensation heat was increased from ambient temperature to the condensation temperature of the methanol (about 120° C. at 6 bar), as shown by measurements of the axial temperature profiles in the catalyst bed. The operating pressure was 8 bar in the evaporator and 6 bar in the DME synthesis reactor. Care was taken to ensure that a maximum temperature difference of 120° C. between the methanol vapor as heating medium and the catalyst temperature was not exceeded at any time, in order to avoid too strong a thermal load of the catalyst.

After about 70% of the catalyst bed had reached the methanol condensation temperature of about 120° C. at 6 bar, the operating pressure in the reactor was raised to 16 bar, corresponding to a condensation temperature of about 160° C. The operating pressure in the methanol evaporator was increased to 18 bar. The methanol evaporated at 18 bar was passed to the reactor, until the entire catalyst had reached the condensation temperature of methanol at 16 bar, i.e. about 160° C.

Methanol condensate produced was collected in a separating device connected to the fixed-bed reactor. The filling level of condensed methanol in the separating device was kept constant by pumping off and recirculation to the methanol evaporator. After the catalyst bed was completely heated up to about 160° C., the liquid methanol condensate in the separating device was drained completely and pumped back to the methanol evaporator via a return conduit.

Drying and further heating of the catalyst without methanol condensation: After the catalyst bed was completely heated up to about 160° C., the pressure in the reactor was reduced to about 3 bar. Then, the catalyst bed was dried at 3 bar with hot methanol vapor of 160° C. by evaporation of methanol bound in and on the catalyst in liquid form. The methanol evaporator continued to operate at 18 bar. The methanol vapor was condensed in a cooler provided downstream of the reactor. In the technical application of the method, the condensation can be effected in the first distillation column downstream of the reactor.

After two hours, the temperature of the methanol evaporated in the evaporator was increased by means of a heat exchanger to about 180° C. and after another two hours to about 200° C. In this way, the catalyst was gently dried and heated up further. Subsequently, the reactor pressure was raised to 10 bar. Two hours later, the temperature was adjusted to 220° C. and the reactor pressure was adjusted to 13 bar.

Starting the DME reaction: At temperatures of 200 to 220° C. the beginning of the reaction of methanol to DME and water was observed. The above-described procedure has avoided the condensation of reaction water in the reactor. The reaction heat released has further heated up the reactor filled with catalyst. For an economic operation of the reactor at an acceptable reaction rate, the reactor inlet temperature is adjusted to between 240 and 280° C.

The reaction products DME and water traversed the catalyst bed and also reached colder regions. In this phase of heating up, the reactor pressure was chosen such that the condensation temperatures of the possible mixtures of methanol, DME and water at the reactor outlet were distinctly below the catalyst temperature. With increasing reactor outlet temperature, the operating pressure in the reactor was raised again, until an operating pressure of about 15 bar was reached.

After exit from the reactor, methanol and later on the reaction product largely was condensed by means of said cooler during the entire start-up phase. The condensate initially consisted of pure methanol and after the beginning of the reaction of methanol-water mixtures. The methanol fraction can be separated in a known way for example by means of distillation and be recirculated to the methanol evaporator. The fraction of the reactor product not condensing in the cooler chiefly consisted of DME and can be supplied to a DME product processing, which in a manner likewise known per se can comprise one or more distillation steps.

Numerical Example

A laboratory experiment was carried out, in order to demonstrate the feasibility of the heating method according to the invention with condensing methanol at a reactor pressure of 10 bar. Heating up should be effected at a fixed end temperature of about 150° C. With reference to ambient temperature, this corresponded to a temperature difference of roughly 120° C. The remaining experimental conditions corresponded to those of the exemplary embodiment described above.

To be able to make a statement as to a possible conversion of methanol to DME, gas samples were taken from the gaseous product stream after cooling for the reactor product. The duration of the experiment was a total of three hours. In the process, a total of 600 g of methanol were supplied to the reactor as vapor. After reaching the end temperature of 150° C., the methanol conversion was 0.013 wt-%. Hence it follows that no significant conversion of methanol to DME does yet take place up to 150° C.

The invention provides a method for starting up a reactor for the production of dimethyl ether (DME) by dehydration of methanol, which can do without any non-process resources and without additional apparatus expenditure. The used heat transfer medium need not be disposed of, but can be converted to the target product DME after completion of the start-up of the DME synthesis reactor.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B, and C" should be interpreted as one or more of a group of elements consisting of A, B, and C, and should not be interpreted as requiring at least one of each of the listed elements A, B, and C, regardless of whether A, B, and C are related as categories or otherwise. Moreover, the recitation of "A, B, and/or C" or "at least one of A, B, or C" should be interpreted as including any singular entity from the listed elements, e.g., A, any subset from the listed elements, e.g., A and B, or the entire list of elements A, B, and C.

The invention claimed is:

1. A method for heating up a catalytic fixed-bed reactor configured to convert methanol to dimethyl ether (DME), the method comprising:
    (a) adjusting a catalytic fixed-bed reactor, comprising a solid catalyst suitable for dehydrating methanol to DME, to an initial temperature of the solid catalyst at a first pressure, at least one temperature measuring device being mounted in the presence of the catalyst;
    (b) evaporating liquid pure methanol in an evaporation device, to obtain a first vaporous pure methanol stream;
    (c) contacting the first vaporous pure methanol stream with the catalyst, until a condensation temperature of the methanol is reached at the first pressure, to obtain a liquid condensate comprising methanol;
    (d) providing the liquid condensate to a separating device, the separating device being in fluid connection with the catalyst, and discharging a condensate stream comprising methanol from the separating device;
    (e) lowering the pressure in the catalytic fixed-bed reactor to a second pressure, the second pressure being below the first pressure, and contacting the catalyst with a second vaporous pure methanol stream suitable for removing condensed methanol, wherein the second vaporous pure methanol stream is superheated with respect to the second pressure;
    (f) heating up the second vaporous pure methanol stream using a heating device, to obtain a vaporous, superheated pure methanol stream, and contacting the vaporous, superheated pure methanol stream with the catalyst, wherein the vaporous, superheated pure methanol stream is heated up to such an extent that in or at the catalyst a fixed end temperature is reached.

2. The method of claim 1, wherein (b) to (d) are repeated several times, and
    wherein the first pressure is increased incrementally.

3. The method of claim 1, wherein the fixed end temperature corresponds to a light-off temperature or starting temperature of dehydrating methanol to DME at the fixed reactor pressure.

4. The method of claim 1, wherein the solid catalyst is in the form of a bed of granular catalyst.

5. The method of claim 1, wherein the solid catalyst comprises alumina.

6. The method of claim 1, further comprising:
    recycling condensed methanol from the separating device to the evaporation device.

7. The method of claim 1, wherein the separating device is integrated into the fixed-bed reactor.

8. A method of producing dimethyl ether (DME) by heterogeneously catalyzed dehydration of a gaseous or vaporous feed stream containing methanol on a solid catalyst active for dehydrating methanol to DME, comprising:
    (a) first, heating up a catalytic fixed-bed reactor by the method of claim 1;
    (b) catalytically converting a feed stream comprising gaseous methanol under dehydration conditions to obtain a product stream comprising DME; and (c) recovering the DME from the product stream comprising the DME.

9. A plant configured to heat up a catalytic fixed-bed reactor configured to convert methanol to dimethyl ether (DME), the plant comprising:
   (a) a fixed-bed reactor comprising a solid methanol dehydration catalyst, a first pressure maintaining device, and a temperature measuring device;
   (b) a methanol evaporation device comprising a second pressure maintaining device;
   (c) a separating device configured to separate liquid condensate comprising methanol, the separating device being in direct fluid connection with the solid methanol dehydration catalyst; and
   (d) a return conduit configured to recirculate liquid condensate comprising methanol from the separating device to the methanol evaporation device, the return conduit being in fluid connection with the separating device and the methanol evaporation device.

10. The plant of claim 9, wherein the separating device is integrated into the fixed-bed reactor.

11. The method of claim 1, wherein the at least one temperature measuring device is mounted in the same space as the catalyst.

12. The method of claim 1, wherein the at least one temperature measuring device is mounted in the catalyst.

13. The method of claim 1, wherein the solid catalyst is present as a catalyst honeycomb.

14. The method of claim 1, wherein the separating device is arranged outside the fixed-bed reactor.

15. The plant of claim 9, wherein the separating device is arranged outside the fixed-bed reactor.

16. The plant of claim 9, wherein the fixed-bed reactor comprises more than one temperature measuring device.

17. The plant of claim 9, wherein the solid methanol dehydration catalyst is in the form of a bed of granular catalyst.

18. The plant of claim 9, wherein the solid methanol dehydration catalyst comprises alumina.

19. The plant of claim 9, wherein the at least one temperature measuring device is mounted in the solid methanol dehydration catalyst.

20. The plant of claim 9, wherein the solid methanol dehydration catalyst is present as a catalyst honeycomb.

21. A plant configured to heat up a catalytic fixed-bed reactor configured to convert methanol to dimethyl ether (DME), the plant comprising:
   (a) a fixed-bed reactor comprising a solid methanol dehydration catalyst, a first pressure maintaining device, and a temperature measuring device;
   (b) a methanol evaporation device comprising a second pressure maintaining device;
   (c) a separating device configured to separate liquid condensate comprising methanol, the separating device being in fluid connection with the solid methanol dehydration catalyst; and
   (d) a return conduit configured to recirculate liquid condensate comprising methanol from the separating device to the methanol evaporation device, the return conduit being in fluid connection with the separating device and the methanol evaporation device,
   wherein the separating device is integrated into the fixed-bed reactor.

* * * * *